(12) United States Patent
Miller et al.

(10) Patent No.: US 11,627,872 B2
(45) Date of Patent: Apr. 18, 2023

(54) FLUID FILTRATION, CLEANING, AND DEFOGGING DEVICE

(71) Applicant: Buffalo Filter LLC, Lancaster, NY (US)

(72) Inventors: Michael J. Miller, Depew, NY (US); William Kellner, Amherst, NY (US); Kyrylo Shvetsov, Depew, NY (US); Greg Pepe, Lancaster, NY (US); Samantha Bonano, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 36 days.

(21) Appl. No.: 17/316,133

(22) Filed: May 10, 2021

(65) Prior Publication Data

US 2021/0259534 A1 Aug. 26, 2021

Related U.S. Application Data

(62) Division of application No. 16/545,385, filed on Aug. 20, 2019, now Pat. No. 11,026,568, which is a
(Continued)

(51) Int. Cl.
*A61B 1/12* (2006.01)

(52) U.S. Cl.
CPC .............. *A61B 1/123* (2013.01); *A61B 1/121* (2013.01); *A61B 1/127* (2013.01); *A61B 1/128* (2013.01);
(Continued)

(58) Field of Classification Search
CPC ...................................................... A61B 1/123
See application file for complete search history.

(56) References Cited

U.S. PATENT DOCUMENTS

| 5,274,874 A | 1/1994 | Cercone et al. |
| 5,880,779 A | 3/1999 | Rhynes |
| (Continued) | | |

FOREIGN PATENT DOCUMENTS

| WO | 2015171771 A1 | 11/2015 |
| WO | 2016115310 A2 | 7/2016 |

OTHER PUBLICATIONS

International Search Report for PCT/US16/60140, dated Dec. 16, 2016, dated Jan. 27, 2017.
(Continued)

*Primary Examiner* — Jason Y Ko
(74) *Attorney, Agent, or Firm* — Timothy W. Menasco, Esq.; Harter Secrest & Emery LLP

(57) ABSTRACT

Presented is a method and apparatus for aiding medical procedures. An apparatus includes a housing defining a first opening, a second opening, and a interior, and a first cleaning element maintained within the interior relative to the first opening, the first cleaning element comprising at least one cleaning agent operable to remove extraneous debris from an object. The apparatus further includes a second cleaning element maintained with the interior relative to the second opening, the second cleaning element comprising at least one cleaning material and at least one white reference material, the at least one cleaning material operable to remove debris from an object. The apparatus also includes a conduit defining a passage from a first end of the housing to a second end of the housing.

9 Claims, 7 Drawing Sheets

Related U.S. Application Data division of application No. 15/341,757, filed on Nov. 2, 2016, now Pat. No. 10,426,327.

(60) Provisional application No. 62/287,817, filed on Jan. 27, 2016, provisional application No. 62/249,613, filed on Nov. 2, 2015.

(52) U.S. Cl.
CPC ..... *A61L 2202/122* (2013.01); *A61L 2202/24* (2013.01)

(56) References Cited

U.S. PATENT DOCUMENTS

| | | |
|---|---|---|
| 8,608,816 B2 | 12/2013 | Palmerton et al. |
| 9,415,160 B2 | 8/2016 | Bonano et al. |
| 2002/0022762 A1 | 2/2002 | Beane et al. |
| 2008/0161646 A1 | 7/2008 | Gomez |
| 2008/0194915 A1 | 8/2008 | Blackhurst et al. |
| 2013/0174525 A1* | 7/2013 | Palmerton ............. A61M 1/784 55/355 |
| 2014/0165842 A1 | 6/2014 | Bonano et al. |
| 2016/0114281 A1 | 4/2016 | Bonano et al. |
| 2016/0135673 A1 | 5/2016 | Miller et al. |

OTHER PUBLICATIONS

European Search Report for Application No. 16862890.7, dated Sep. 27, 2019.

* cited by examiner (A) PROVIDING A HOUSING DEFINING A FIRST OPENING, A SECOND OPENING, AND AN INTERIOR; (B) PROVIDING A FIRST CLEANING ELEMENT MAINTAINED WITHIN THE INTERIOR RELATIVE TO THE FIRST OPENING, THE FIRST CLEANING ELEMENT COMPRISING AT LEAST ONE CLEANING AGENT OPERABLE TO REMOVE EXTRANEOUS DEBRIS FROM AN OBJECT; (C) PROVIDING A SECOND CLEANING ELEMENT MAINTAINED WITH THE INTERIOR RELATIVE TO THE SECOND OPENING, THE SECOND CLEANING ELEMENT COMPRISING AT LEAST ONE CLEANING MATERIAL AND AT LEAST ONE WHITE REFERENCE MATERIAL, THE AT LEAST ONE CLEANING MATERIAL OPERABLE TO REMOVE DEBRIS FROM AN OBJECT; AND (D) PROVIDING A CONDUIT DEFINING A PASSAGE FROM A FIRST END OF THE HOUSING TO A SECOND END OF THE HOUSING, THE CONDUIT COMPRISING AT LEAST ONE FILTER AND AT LEAST ONE LIQUID TRAP, THE CONDUIT OPERABLE TO ALLOW A FLOW FROM THE FIRST END OF THE HOUSING TO THE SECOND END OF THE HOUSING AND TO REMOVE DEBRIS FROM THE FLOW.
— 1302

WHEREIN THE HOUSING FURTHER COMPRISES A MICROFIBER MATERIAL FIXEDLY ATTACHED AN OUTSIDE SURFACE OF THE HOUSING
— 1304

WHEREIN THE FIRST OPENING IS OCCLUDED BY A FIRST FRANGIBLE DISC OPERABLE TO MAINTAIN THE AT LEAST ONE CLEANING AGENT WITHIN THE FIRST OPENING, AND WHEREIN THE SECOND OPENING IS OCCLUDED BY A SECOND FRANGIBLE DISC
— 1306

THE CONDUIT FURTHER COMPRISING A FLOW SELECTOR OPERABLE TO CHANGE A RATE OF FLOW OF FLUID THROUGH THE CONDUIT
— 1308

THE FIRST OPENING AND THE SECOND OPENING EACH COMPRISING AT LEAST ONE ILLUMINATION DEVICE OPERABLE TO AT LEAST PARTIALLY INDICATE A LOCATION OF THE FIRST OPENING AND THE SECOND OPENING
— 1310

THE METHOD FURTHER COMPRISING PROVIDING A POWER SOURCE OPERABLY COUPLED TO AN ELECTRICAL RESISTANCE ELEMENT, THE ELECTRICAL RESISTANCE ELEMENT OPERABLE TO HEAT THE INTERIOR
— 1312

WHEREIN THE ELECTRICAL RESISTANCE ELEMENT IS A PRINTED CIRCUIT BOARD (PCB)
— 1314

WHEREIN THE AT LEAST ONE CLEANING AGENT IS A POROUS MATERIAL OPERABLE TO RECEIVE AND HOLD A CLEANING SOLUTION
— 1316

WHEREIN THE AT LEAST ONE CLEANING MATERIAL IS A PAIR OF SPONGES, AND THE AT LEAST ONE WHITE REFERENCE MATERIAL FORMS A V-SHAPE OPERABLE TO ACCEPT A SCOPE
— 1318

FIG. 13

FLUID FILTRATION, CLEANING, AND DEFOGGING DEVICE

CROSS-REFERENCE TO RELATED APPLICATIONS

The present application is a divisional application of U.S. patent application Ser. No. 15/341,757 filed on Nov. 2, 2016, and which claims the benefit of U. S. Provisional Patent Application Nos. 62/287,817 filed on Jan. 27, 2016 and 62/249,613 filed on Nov. 2, 2015, the specifications of which are hereby incorporated by reference in their entirety.

BACKGROUND OF THE INVENTION

Field of the Invention

The present disclosure provides a method and apparatus for aiding medical procedures. More particularly, embodiments of the present disclosure provide a filtration, cleaning, and defogging device for aiding surgical or medical procedures.

Description of Related Art

A laparoscope or endoscope is used in conjunction with a camera system for visualization during surgical procedures. When the scope is introduced from ambient room temperature into a cavity at body temperature, the rapid change causes the lens to fog. During surgery, the introduction of surgical tools such as an electrosurgical device deliver energy, creating heat, and vaporizes the intracellular fluid, which increases the pressure inside the cell and eventually causes the cell membrane to burst. When this happens, a plume of smoke containing mostly water vapor is created, along with the aeration of cellular debris. During procedures involving a scope, many times this water vapor, smoke plume, and/or cellular debris attach to the lens, impairing the view of the surgical site.

BRIEF SUMMARY OF THE INVENTION

In view of the foregoing, it is an object of the present disclosure to provide an apparatus and method for aiding medical procedures.

A first exemplary embodiment of the present disclosure provides an apparatus for aiding medical procedures. The apparatus includes a housing defining a first opening, a second opening, and an interior, and a first cleaning element maintained within the interior relative to the first opening, the first cleaning element comprising at least one cleaning agent operable to remove extraneous debris from an object. The apparatus further includes a second cleaning element maintained with the interior relative to the second opening, the second cleaning element comprising at least one cleaning material and at least one white reference material, the at least one cleaning material operable to remove debris from an object. The apparatus still further includes a conduit defining a passage from a first end of the housing to a second end of the housing, the conduit comprising at least one filter and at least one liquid trap, the conduit operable to allow a flow from the first end of the housing to the second end of the housing and to remove debris from the flow.

A second exemplary embodiment of the present disclosure provides a method of aiding medical procedures. The method includes providing a housing defining a first opening, a second opening, and an interior, and providing a first cleaning element maintained within the interior relative to the first opening, the first cleaning element comprising at least one cleaning agent operable to remove extraneous debris from an object. The method further includes providing a second cleaning element maintained with the interior relative to the second opening, the second cleaning element comprising at least one cleaning material and at least one white reference material, the at least one cleaning material operable to remove debris from an object. The method still further includes providing a conduit defining a passage from a first end of the housing to a second end of the housing, the conduit comprising at least one filter and at least one liquid trap, the conduit operable to allow a flow from the first end of the housing to the second end of the housing and to remove debris from the flow.

A third exemplary embodiment of the present disclosure provides an apparatus for filtration, cleaning, and defogging. The apparatus includes a first housing comprising a cleaning element maintained within the first housing, the cleaning element a cleaning fluid operable to remove debris from an object, the cleaning element occluded within the housing by at least one frangible disc. The apparatus further includes a second housing comprising a filtration conduit through a passage within the second housing, the second housing operable to be removeably coupled to the first housing, The filtration conduit comprising a filter and a liquid trap, the filtration conduit operably coupled to a flow selector operable to regulate a flow of fluid through the filtration conduit.

The following will describe embodiments of the present disclosure, but it should be appreciated that the present disclosure is not limited to the described embodiments and various modifications of the invention are possible without departing from the basic principle. The scope of the present disclosure is therefore to be determined solely by the appended claims.

BRIEF DESCRIPTION OF THE SEVERAL VIEWS OF THE DRAWING(S)

FIG. 13 is a logic flow diagram in accordance with a method and apparatus for performing exemplary embodiments of this disclosure.

DETAILED DESCRIPTION OF THE INVENTION

Figure 1:
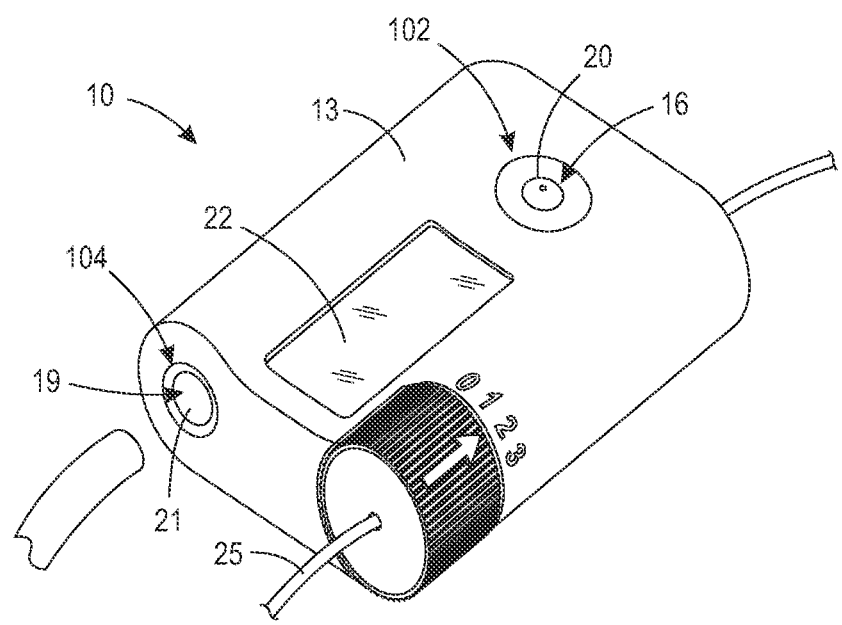
FIG. 1 is a perspective view of a first embodiment of a device suitable for use in practicing exemplary embodiments of this disclosure.

At the outset, it should be clearly under stood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal.", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Embodiments of the present disclosure provide a device operable to interact with medical or surgical devices or tools (e.g., a scope for laparoscopic or endoscopic procedures, trocars, scalpels, and the like) such that the medical or surgical tools can be cleaned and/or defogged to aid in medical or surgical procedures. Embodiments of the present disclosure also provide a device operable to filter a flow of fluid from a patient's body (e.g., smoke or vapor from a patient's body cavity produced during surgery). Embodiments further provide a white balance for improved video/pictures from a scope during surgical or medical procedures. Embodiments of surgical or medical procedures include laparoscopy, endoscopy, arthroscopy, bronchoscopy, colonoscopy, cystoscopy, enteroscopy, hysteroscopy, laryngoscopy, mediastinoscopy, ureteroscopy, and other procedures involving a scope in a body cavity.

Referring now to the drawings, and more particularly to FIG. 1 thereof, embodiments of the present disclosure provide a fluid filtration, cleaning and defogging device 10. In one embodiment, the device 10 includes a housing 13. The housing 13 has a first opening 16 for receiving a medical/surgical scope in a generally vertically oriented position and a second opening 19 for receiving a scope in a generally horizontally oriented position. An illumination element 102, 104 or a plurality of illumination devices, such as light emitting diodes, may be disposed around the openings 16, 19 to indicate a location of openings 16 and 19 on housing 13 to facilitate insertion of the surgical scopes and other medical devices in darker environments. Illumination devices 102, 104 may also be used to indicate when the device 10 is ready for use. Illumination devices 102, 104 may also be used to indicate the flow setting for the filtration portion of the device 10. In certain embodiments, the openings 16, 19 may be sealed by a frangible disc 20, 21 made of an elastomeric material or the like. The frangible discs 20, 21 are provided to seal openings 16, 19 along with a cleaning solution in the device prior to use. The housing 13 is closed and sealed to protect the internal components from exposure to outside elements. A microfiber wipe 22 may be mounted to the exterior of the housing 13 such that a scope may be brought into contact with the wipe 22 to remove debris. This embodiment utilizes separate compartments to clean, warm and white balance a scope.

Figure 4:
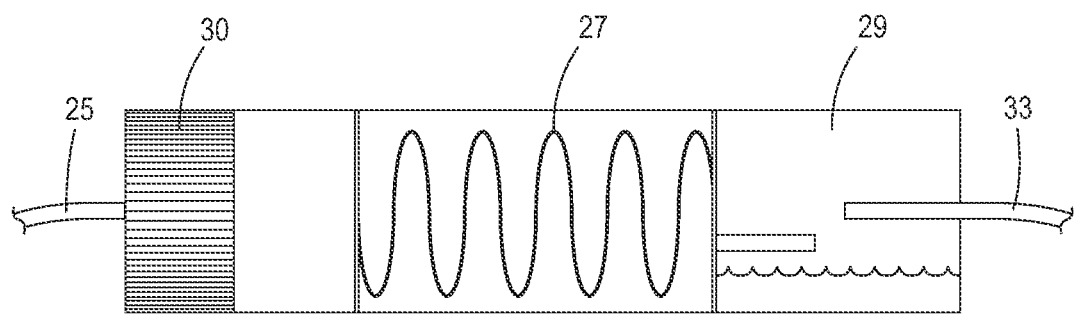
FIG. 4 is a side view of the first embodiment of the device suitable for use in practicing exemplary embodiments of this disclosure.

The first embodiment of the device 10 also provides for fluid filtration. A conduit or tube 25 provides for an input passageway to a filter system disposed in the housing 13. The conduit 25 may be provided with a luer lock (not shown) that attaches to a conduit or trocar leading to a pressurized surgical site such as a laparascopy with a pneumoperitoneum. As shown in FIG. 4, the conduit 25 leads to a liquid trap 29. Embodiments of liquid trap 29 are operable to remove liquid such as condensed water vapor from a gas. Carbon or other odor removing media and particulate filters 27 are disposed inside the housing 13. Embodiments of filters 27 allow a flow of air or fluid through conduit 25 while removing extraneous materials or debris from the air or fluid. A flow selector 30 is disposed on the exterior of the housing 13. A second conduit or tube 33 extending from the opposite end of the housing 13 may be disposed in fluid communication with either a vacuum system or with atmosphere. The system may be manually or automatically switched between connection to a vacuum source or venting to atmosphere. The flow selector 30 provides for adjustment of the flow through the filtration device without deflating the peritoneal cavity.

Figure 2:
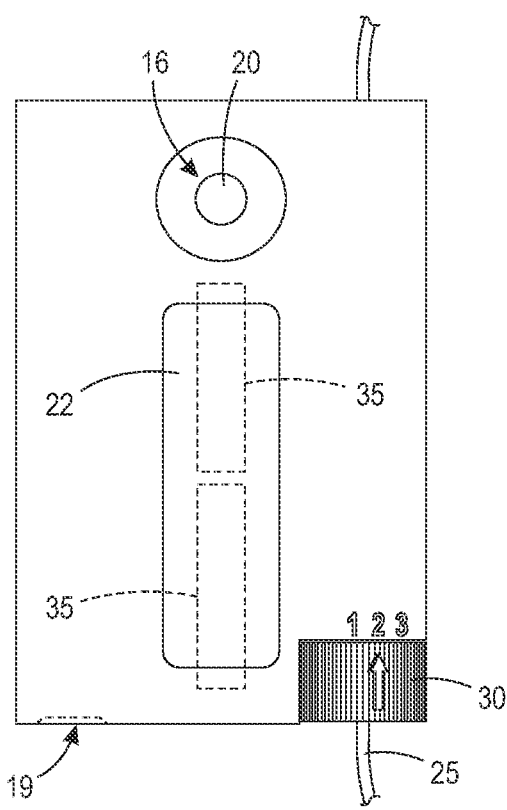
FIG. 2 is a top plan view of the first embodiment of the device suitable for use in practicing exemplary embodiments of this disclosure.
Figure 3:
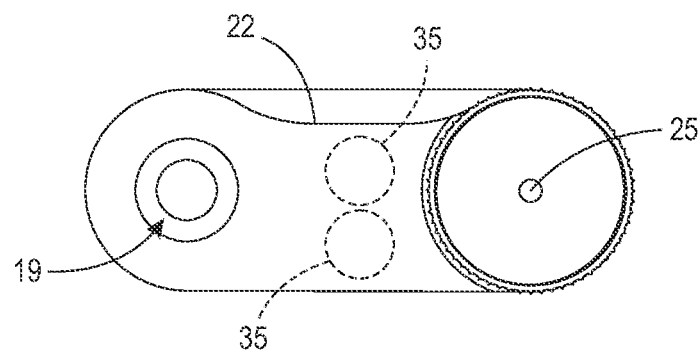
FIG. 3 is an end view of the first embodiment of the device suitable for use in practicing exemplary embodiments of this disclosure.

As shown in FIGS. 2-3, the first embodiment of the device may be provided with a power source such as one or more batteries 35. As shown the batteries 35 may be installed within housing 13 at a mid-portion of the device 10. The batteries 35 may be provided in a circuit for providing heat through electrical resistance in a printed circuit board (PCB). The circuit board may be designed to have multiple and separate heater sections built into the circuit. The circuit may be rigid or flexible. The device may be provided with an electronic control circuit to maintain PCB temperature of the heating circuit for warming the cleaning fluid. Also, the heating element can be a dedicated component separate from the circuit board. The heating element may be flexible or ridged to allow for a bundle of wire to be around the port to provide a heater. Heating can be provided to one or both ports or openings 16, 19 and may have independent temperatures.

Figure 5:
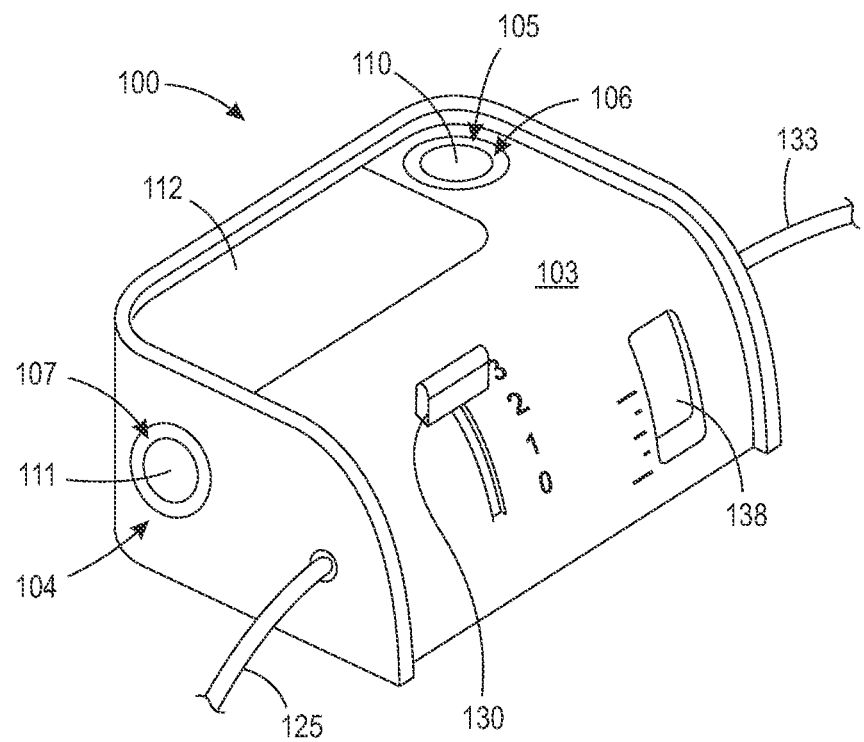
FIG. 5 is a perspective view of a second embodiment of a device suitable for use in practicing exemplary embodiments of this disclosure.

An alternate embodiment is shown in FIG. 5. Shown in FIG. 5 is device 100, which includes a housing 103. The housing 103 has a first opening 106 for receiving a scope in a generally vertically oriented position, and a second opening 109 for receiving a scope in a generally horizontally oriented position. A plurality of illumination devices 105, 107, such as light emitting diodes, may disposed around the openings 106, 109 to facilitate insertion of the surgical scopes in darker environments. In certain embodiments, the openings 106, 109 may be sealed by a frangible disc 110, 111 made of an elastomeric material or the like. The frangible discs 110, 111 are provided to seal a cleaning solution in the device prior to use. The housing 103 is closed and sealed to protect the internal components from exposure to outside elements. A microfiber wipe 112 may be mounted to the exterior of the housing 103 such that a scope may be brought into contact with the wipe to remove debris and/or extraneous material. This embodiment utilizes separate compartments to clean, warm and white balance a scope.

The device 100 also provides for fluid filtration. A conduit or tube 125 provides for an input passageway to a filter system disposed in the housing 103. The conduit 125 may be provided with a luer lock (not shown) that attaches to a conduit or trocar leading to a pressurized surgical site such as a laparascopy with a pneumoperitoneum. The conduit 125 leads to a liquid trap 129 operable to remove liquid from a gas. Carbon or other odor removing media and particulate filters 127 are disposed inside the housing 103. A flow selector 130 is disposed on the exterior of the housing 103. Embodiments of flow selector 130 are operable to regulate and change upon user input a flow of gas or fluid through conduit 25. A conduit or tube 133 extending from the opposite end of the housing 103 may be disposed in fluid communication with either a vacuum system or with atmosphere. The system may be manually or automatically switched between connection to a vacuum source or venting to atmosphere. In the embodiment shown in FIG. 5, the housing 103 also includes a window 138 for viewing levels of liquid trapped in liquid trap 129.

Figure 6:
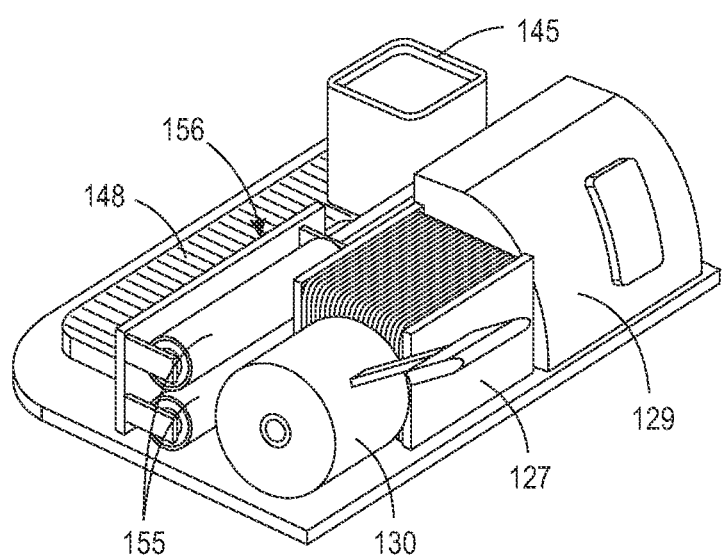
FIG. 6 is a perspective view of the second embodiment of the device with the housing removed suitable for use in practicing exemplary embodiments of this disclosure.

Turning to FIG. 6, with the housing 103 removed for clarity, the flow selector 130 provides for adjustment of the flow through the filtration device without deflating the peritoneal cavity. The filter(s) 127 are disposed in alignment with the flow selector and may be positioned between the flow selector 130 and the liquid trap chamber 129. On the other side of the figure, a cavity 145 may be formed to receive the scope vertically through the first opening 106. A cleaning material may be disposed at the bottom of the cavity. The cleaning material may comprise a sponge or other soft, porous material for receiving and holding a cleaning solution. Adjacent to the cavity 145, a horizontal bed 148 provides for support of a horizontally disposed scope that is inserted through the second opening 109.

A power source such as one or more batteries 155 may be mounted in a middle portion of the assembly. The power source may be used to provide power to a heater for the warming fluid for the scope. The batteries 155 may be provided in a circuit for providing heat through electrical resistance in a printed circuit board 156. The circuit board 156 may be designed to have multiple and separate heater sections built into the circuit. The circuit board 156 may be rigid or flexible. The device may be provided with an electronic control circuit to maintain printed circuit board (PCB) 156 temperature of the heating circuit for warming the cleaning fluid maintained within cavity 145 and/or horizontal bed 148. In another embodiment, device 100 can include a heating element (e.g., a resistance heating element) that is a dedicated component separate from the circuit board operable to provide heat to the cleaning fluid maintained within the cavity 145 and/or horizontal bed 148. The heating element may be flexible or ridged to allow for a bundle of wire to be around the port to provide a heater. Heating can also be provided to one or both ports and may have independent temperatures. Embodiments of circuit board 156 and/or a heating element are operable to heat or warm the cleaning fluid maintained within the cavity 145 and/or horizontal bed 148 such that there is not a substantial temperature change between the heated cleaning fluid and an interior of a body cavity.

Figure 7:
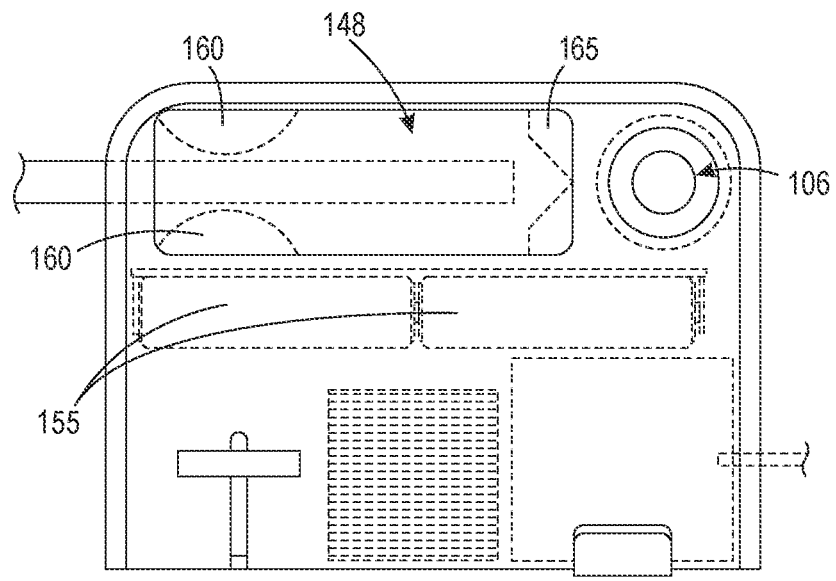
FIG. 7 is a top plan view of the second embodiment of the device suitable for use in practicing exemplary embodiments of this disclosure.

Turning to FIG. 7, the horizontally disposed portion of the cleaning device may contain a sponge or pair of sponges or a cleaning material 160 that is split to provide a channel for sliding the scope through the cleaning material. The two sponges 160 are configured to accept and to warm scopes 180, 185 (shown in FIG. 8) of all sizes. A V-shaped white reference material 165 may be disposed at the end of the cavity 148. The white balance reference material 165 is constructed of a non-porous material such as silicone. The white balance reference material 165 does not hold any liquid or cleaning solution and is arranged to provide a white balance for providing a reference color for optimizing the camera. The white balance reference material 165 is V-shaped so that scopes having different diameters may be inserted through the cleaning material 160 and into contact with the white balance reference material 165.

Figure 8:
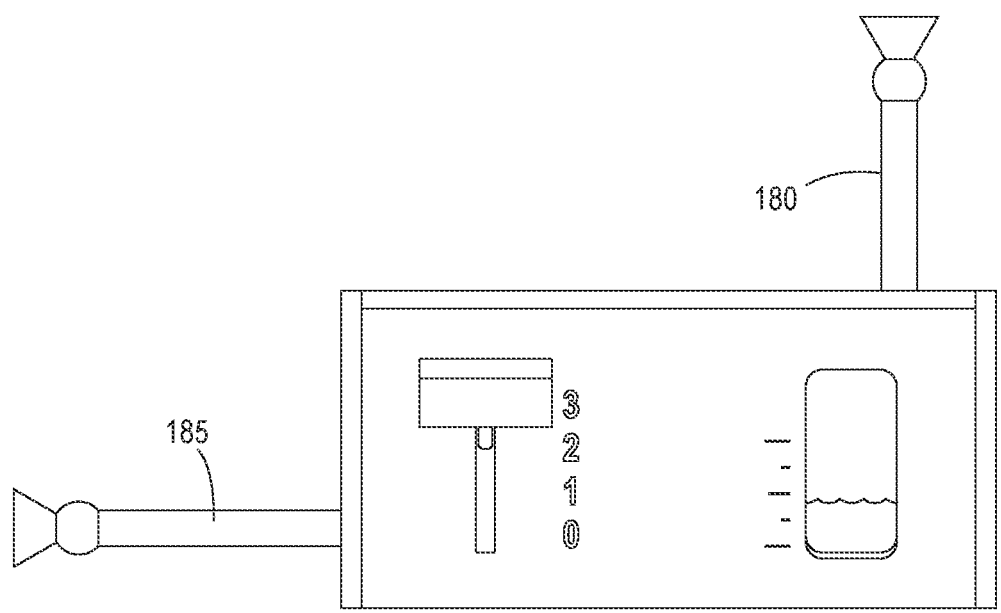
FIG. 8 is a side view of the second embodiment of the device shown in use with a pair of scopes suitable for use in practicing exemplary embodiments of this disclosure.
Figure 9:
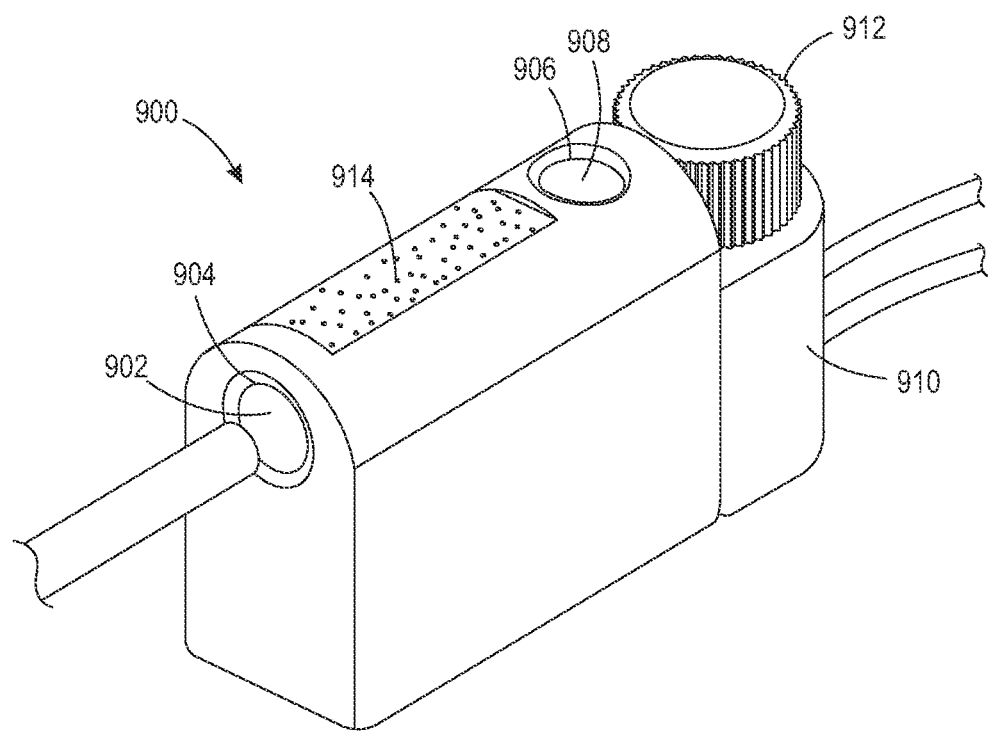
FIG. 9 is a top perspective view of a third embodiment of a device suitable for use in practicing exemplary embodiments of this disclosure.

Reference is now made to FIG. 8, which depicts a side view of the device 100 with a first scope 180 being warmed via the first opening 106 and a second scope 185 being cleaned and white balanced via the second opening 109.

Figure 10:
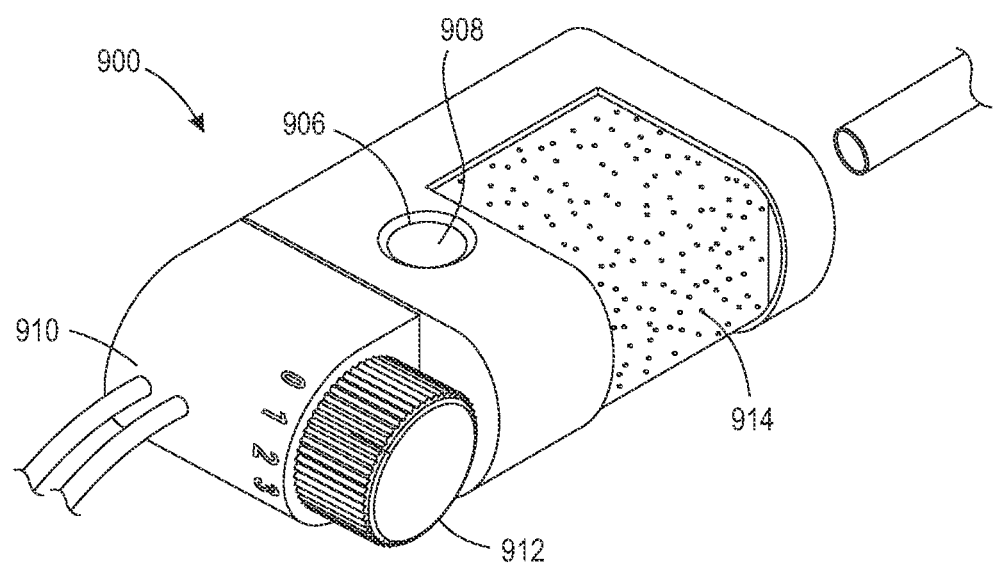
FIG. 10 is side perspective view of the third embodiment of the device suitable for use in practicing exemplary embodiments of this disclosure.

Turning to FIGS. 9-12, illustrated is an alternative embodiment of the fluid filtration and cleaning and defogging device 900. The device 900 as shown in FIGS. 9-12 is similar to the device illustrated in FIG. 1 and may be equipped with any of the parts, features, designs, and/or functionality as described hereinabove with reference to FIGS. 1-8. Shown in FIGS. 9-12 is device 900 having a first opening 902 occluded by a frangible disc 904 operable to maintain a cleaning fluid. Device 900 also includes a second opening 906 occluded by a frangible disc 908 operable to maintain a cleaning material, a conduit 910 having a filter and liquid trap. In FIG. 10, second opening 906 with frangible disc 908 is shown located on a side face of device 900. Conduit 910 operable to be removeably coupled to a surgical site to pass gas or fluid from within a body cavity through conduit 910. It should be noted that in the embodiment illustrated in FIGS. 9-12, the input and output of conduit 910 is located adjacent to one another. The flow of gas or fluid through conduit 910 can be operably regulated, changed or maintained by flow selector 912. Also shown is wipe 914 operable to remove extraneous material or debris from an opposing object, such as a medical or surgical tool. Embodiments of device 900 also include a heating element operable to heat the cleaning fluid and cleaning materials within device 900.

Figure 11:
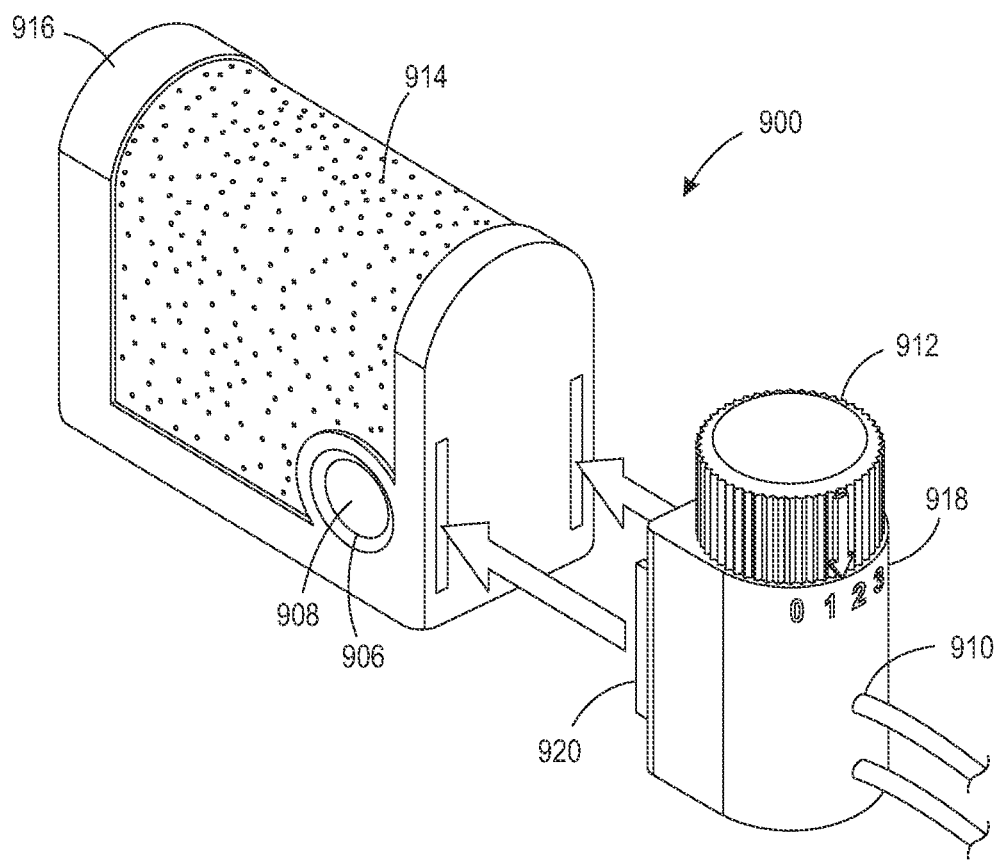
FIG. 11 is perspective view of the third embodiment of the device in separated form suitable for use in practicing exemplary embodiments of this disclosure.
Figure 12:
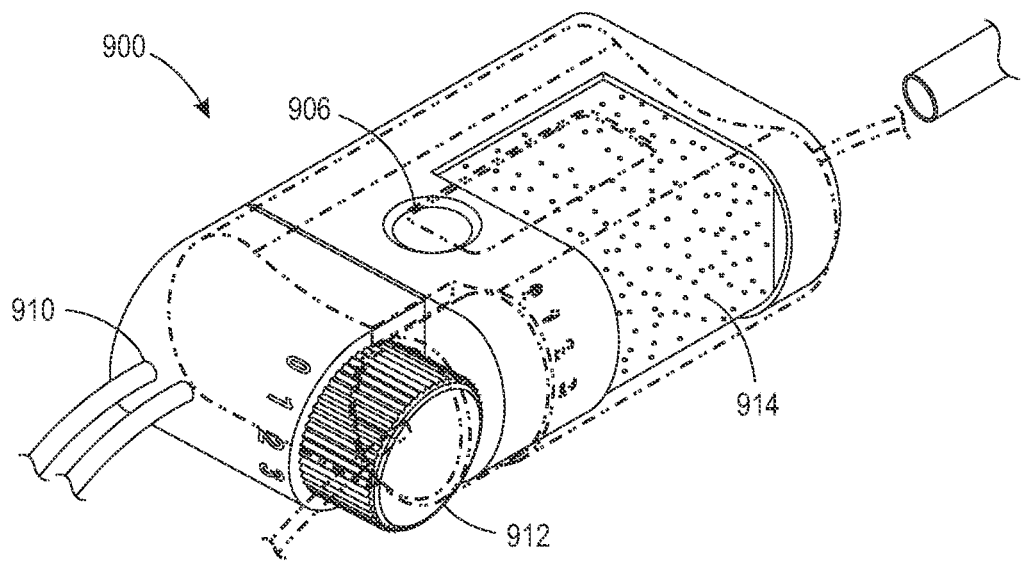
FIG. 12 is a perspective view of the third embodiment of the device suitable for use in practicing exemplary embodiments of this disclosure.

This alternative embodiment, however further provides for a fluid filtration, cleaning, and defogging device having a modular design. In particular, as can be seen in FIG. 11, the device housing as discussed with reference to FIG. 1 may be divided into two detachable and self-contained housings that can be either joined together into a single unit or used separately as distinct devices, as desired by the user. Preferably, a first housing portion 916 may be dedicated to providing a laparoscopic warming device, while a second housing portion 918 may be dedicated to providing a peritoneal plume evaluator. While FIG. 11 illustrates a first housing portion 916 attachable to a second housing portion 918 by a clip 920, it is anticipated that any appropriate coupling mechanism (e.g., snap, clasp, lock, rib, etc.) may be used. It is further anticipated that power and/or electrical signals may be passed between a first housing portion and a second housing portion via the coupling mechanism 920.

Reference is now made to FIG. 13, which depicts a simplified block diagram in accordance with an exemplary method of aiding medical procedures. The process begins at block 1302 which states (a) providing a housing defining a first opening, a second opening, and an interior; (b) providing a first cleaning element maintained within the interior relative to the first opening, the first cleaning element comprising at least one cleaning agent operable to remove extraneous debris from an object; (c) providing a second cleaning element maintained with the interior relative to the second opening, the second cleaning element comprising at least one cleaning material and at least one white reference material, the at least one cleaning material operable to remove debris from an object; and (d) providing a conduit defining a passage from a first end of the housing to a second end of the housing, the conduit comprising at least one filter and at least one liquid trap, the conduit operable to allow a flow from the first end of the housing to the second end of the housing and to remove debris from the flow. Then block 1304 indicates wherein the housing further comprises a microfiber material fixedly attached to an outside surface of the housing.

Some of the non-limiting implementations detailed above are also summarized at FIG. 13 following block 1304. Block 1306 relates to wherein the first opening is occluded by a first frangible disc operable to maintain the at least one cleaning agent within the first opening, and wherein the second opening is occluded by a second frangible disc. Block 1308 then states the conduit further comprising a flow selector operable to change a rate of flow of fluid through the conduit. Block 1310 goes on to state the first opening and the second opening each comprising at least one illumination device operable to at least partially indicate a location of the first opening and the second opening. Block 1312 then indicates the method further comprising providing a power source operably coupled to an electrical resistance element, the electrical resistance element operable to heat the interior.

Block 1314 then relates wherein the electrical resistance element is a printed circuit board (PCB). Block 1316 states wherein the at least one cleaning agent is a porous material operable to receive and hold a cleaning solution. Finally, block 1318 indicates wherein the at least one cleaning material is a pair of sponges, and the at least one white reference material forms a V-shape operable to accept a scope.

The logic diagram on FIG. 13 may be considered to illustrate the operation of a method, or a result of execution of computer program instructions stored in a computer-readable medium. The logic diagram of FIG. 13 may also be considered a specific manner in which components of a device are configured to cause that device to operate, whether such device is a medical or surgical device or some other related device, or one or more components thereof.

Embodiments of the present invention may be provided with any of the aspects and features of the fluid filtration system as described in U.S. patent application Ser. No. 14/884,544, filed on Oct. 15, 2015, entitled "Fluid Filtration Device and System", the disclosure of which is hereby incorporated by reference. Embodiments of the device may also be provided with any of the aspects and features of the cleaning and defogging device as described in U.S. patent application Ser. No. 14/779,986 filed May 6, 2015, entitled "Laparascope and Endoscope Cleaning and Defogging Device", the disclosure of which is hereby incorporated by reference.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An apparatus for filtration, cleaning, and defogging, the apparatus comprising:
    (a) a first housing comprising a cleaning element maintained within the first housing, the cleaning element comprising a cleaning fluid operable to remove debris from an object, the cleaning element occluded within the housing by at least one frangible disc; and
    (b) a second housing comprising a filtration conduit through a passage within the second housing, the second housing operable to be removeably coupled to the first housing, the filtration conduit comprising a filter and a liquid trap operable to remove debris from a flow through the filtration conduit, the filtration conduit operably coupled to a flow selector operable to regulate a flow of fluid through the filtration conduit.

2. The apparatus according to claim 1, wherein the first housing further comprises a microfiber material fixedly attached to an outside surface of the first housing.

3. The apparatus according to claim 1, the apparatus further comprising a power source operably coupled to an electrical resistance element, the electrical resistance element operable to heat an interior of the first housing.

4. The apparatus according to claim 1, wherein the first housing is removeably coupled to the second housing by one of a snap, clasp, lock or rib mechanism.

5. The apparatus according to claim 1, wherein power and electrical signals are operable to pass between the first housing and the second housing.

6. The apparatus according to claim 1, wherein the cleaning element comprises a first opening occluded by the at least one frangible disc operable to maintain a cleaning fluid.

7. The apparatus according to claim 1, the apparatus further comprising a power source operably coupled to an electrical resistance element, the electrical resistance element operable to heat an interior of the first housing.

8. The apparatus according to claim 7, wherein the electrical resistance element is a printed circuit board.

9. The apparatus according to claim 2, where the cleaning element comprises at least one illumination device operable to at least partially indicate a location of the cleaning, element.

\* \* \* \* \*